United States Patent
Proksa

(10) Patent No.: US 7,852,978 B2
(45) Date of Patent: Dec. 14, 2010

(54) IMAGING SYSTEM FOR IMAGING AN OBJECT

(75) Inventor: Roland Proksa, Hamburg (DE)

(73) Assignee: Koninklijke Phillips Electronics N.V., Eindhoven (NL)

( * ) Notice: Subject to any disclaimer, the term of this patent is extended or adjusted under 35 U.S.C. 154(b) by 32 days.

(21) Appl. No.: 12/446,766

(22) PCT Filed: Oct. 24, 2007

(86) PCT No.: PCT/IB2007/054315

§ 371 (c)(1),
(2), (4) Date: Apr. 23, 2009

(87) PCT Pub. No.: WO2008/050298

PCT Pub. Date: May 2, 2008

(65) Prior Publication Data

US 2009/0266994 A1    Oct. 29, 2009

(30) Foreign Application Priority Data

Oct. 27, 2006   (EP) ................... 06123092

(51) Int. Cl.
*A61B 6/00* (2006.01)
(52) U.S. Cl. .............. 378/4; 378/19; 378/901
(58) Field of Classification Search .......... 378/4–20, 378/901
See application file for complete search history.

(56) References Cited

U.S. PATENT DOCUMENTS

| 5,533,080 A | 7/1996 | Pelc |
| 2003/0003054 A1 | 1/2003 | McDonald et al. |
| 2006/0014938 A1 | 1/2006 | Groman et al. |

OTHER PUBLICATIONS

Llopart, X., et al.; Medipix2: a 64-k Pixel Readout Chip with 55-um Square Elements Working in Single Photon Counting Mode; 2002; IEEE Trans. on Nuclear Science; 49(5)2279-2283.

Llopart X., et al.; First test measurements of a 64k pixel readout chip working in single photon counting mode; 2003; Nuclear Instruments and Methods in Physics Research; A 509:157-163.

Ohnesorge, B., et al.; Efficient correction for CT image artifacts caused by objects extending outside the scan field of view; 2000; Med. Phys.; 27(1)39-46.

*Primary Examiner*—Courtney Thomas

(57) ABSTRACT

The present invention relates to an imaging system for imaging an object (20) comprising a polychromatic radiation source (2) and an energy resolving radiation detector (6). The imaging system comprises further a driving device for moving the object (20) and the radiation source (2) relatively to each other, in order to acquire truncated projections from different directions. A calculation unit determines a k-edge component at least of one of the object (20) and a substance within the object (20) from the truncated projections and determines non-truncated projections from the determined k-edge component. A reconstruction unit constructs the object using the non-truncated projections.

11 Claims, 4 Drawing Sheets

IMAGING SYSTEM FOR IMAGING AN OBJECT

FIELD OF THE INVENTION

The present invention relates to an imaging system, an imaging method and a computer program for imaging an object. The invention relates further to a corresponding image generation device, image generation method and computer program for generating an image of an object.

BACKGROUND OF THE INVENTION

Known imaging systems, which acquire truncated projections of an object, reconstruct an image by using these truncated projections. This leads to image artefacts. These known imaging systems use interpolation techniques in order to generate non-acquired missing data and to complete a truncated projection to obtain a non-truncated projection. These calculated non-truncated projections are only approximations so that an image, which has been reconstructed using these calculated non-truncated projections, comprises artefacts.

In "Efficient correction for CT image artefacts caused by objects extending outside the scan field of view", B. Ohnesorge, T. Flohr, K. Schwarz, J. P. Heiken and K. T. Bae, Med. Phys. 27(1), pp. 39-46 (2000), it has also been proposed to backproject the truncated projection using adapted backprojection filters, but these adapted backprojection filters do also generate artefacts in the reconstructed images.

SUMMARY OF THE INVENTION

It is an object of the present invention to provide an imaging system, which generates images by using truncated projections, wherein these images comprise less artefacts than images generated by known imaging systems using truncated projections, i.e. which generates images of improved image quality. Furthermore, a corresponding imaging method, a corresponding image generation device and a corresponding image generation method shall be provided.

In a first aspect of the present invention an imaging system for imaging an object is provided, comprising:
a polychromatic radiation source for emitting polychromatic radiation,
an energy-resolving radiation detector for obtaining detection signals depending on the radiation after passing through the object,
a driving device for moving the object and the radiation source relatively to each other, in order to acquire truncated projections from different directions, wherein the truncated projections comprise the detection signals,
a calculation unit for determining a k-edge component at least of one of the object and a substance within the object from the truncated projections and for determining non-truncated projections from the determined k-edge component,
a reconstruction unit for reconstructing the object using the non-truncated projections.

The step of reconstructing the object can be a step of reconstructing the object itself, for example the material or tissue of the object itself, or a step of reconstructing a substance filled in the object, wherein the object is, for example, a casing or vessel, in which the substance has been filled, and wherein the reconstructed image of the object, e.g. the casing or vessel, is the image of the substance within the object. For example, the reconstructed image of a contrast agent within vessels of a human heart is the reconstructed image of the vessels of the human heart (coronary angiography). If a k-edge component is determined only of the object, a substance does not have to be present within the object.

The invention is based on the idea that a k-edge component at least of one of the object and a substance within the object can be determined from the truncated projections and that non-truncated projections can be determined from the k-edge components. Since an image is reconstructed using only the determined non-truncated projections, the reconstructed images show less artifacts than images, which have been reconstructed by known imaging systems using truncated projections, i.e. the image quality is improved in comparison to known imaging systems using truncated projections.

The calculation unit is preferably adapted for determining the k-edge component by solving a system of equations describing detection signals of the truncated projections as a combination of the k-edge effect at least of one of the object or of a substance within the object, the photo-electric effect and the Compton effect, each contributing with a corresponding component to the detection signals. In particular, the energy-resolving radiation detector provides a number of energy resolved detection signals of different energy bins. These different energy bins comprise preferentially different spectral sensitivities, in particular, each energy bin being a section of the complete energy range in which the detection signal is available and of interest. The attenuation of the radiation, after the radiation has passed at least one of the object or a substance within the object, is preferentially modelled as a combination of the photo-electric effect with a first spectrum, the compton effect with a second spectrum and the remaining attenuation of at least one of the object or a substance within the object with a k-edge in the interesting energy range with a third spectrum (k-edge effect). The density length product for each of the components in each detection signal is modelled as a discrete linear system which is solved to obtain at least the k-edge component at least of one of the object and a substance within the object. From the k-edge component at least of one of the object and a substance within the object non-truncated projections can be determined, which are used to reconstruct the object. The reconstruction can be performed by a conventional reconstruction method. The use of such a system of equations allows to determine k-edge components from the detection signals, i.e. from the truncated projections, and to determine from the k-edge components non-truncated projections having a high quality, wherein the quality of the artefacts in the reconstructed images is further improved.

A system of equations for the plurality of energy-resolved detection signals is preferably solved by used of a numerical method. A preferred method is a maximum likelihood approach that takes noise statistics of the measurement into account.

In a further preferred embodiment a model is used which takes account of an emission spectrum of the radiation source and the spectral sensitivity of the detector. This leads to a higher accuracy of the calculated components and, thus, of the determined non-truncated projections and, therefore, finally to a further improved quality of the reconstructed images.

In a preferred embodiment, the polychromatic radiation source is a polychromatic X-ray source, and the energy-resolving radiation detector is an energy resolving X-ray detector. The use of an X-ray source and of an X-ray detector allows to acquire truncated projections having a signal-two-noise-ratio, which allows to determine k-edge components and therefore non-truncated projections and images reconstructed by using these non-truncated projections, having a further improved quality.

It is preferred that the imaging system is adapted for imaging the object being a first object present within a second object, wherein the polychromatic radiation source is adapted for illuminating only the first object such that truncated projections are acquired, which are sufficient to reconstruct the first object. Since only the first object is illuminated such that truncated projections are acquired which are sufficient to reconstruct the first object, the overall dose given to the object, which is for example a patient, is reduced. Alternatively, the intensity of the radiation can be increased without increasing the overall dose, because, in this embodiment, the illumination has been limited such that truncated projections are acquired, which are sufficient to reconstructed the first object only. If known imaging systems limit the illumination in the same way, images can only be reconstructed using truncated projections leading to images of poor quality. If the quality of images generated by known imaging systems shall be increased, the illumination geometry has to be modified such that only non-truncated projections are acquired, i.e. the radiation source has to be adapted for illuminating the first object and the second object such that only non-truncated projections of these two objects are acquired, but this leads to a dose given to the object, for example, given to the patient, which is unacceptable, if only the first object has to be reconstructed. In contrast, this preferred embodiment according to the invention allows to generate high quality images of the first object without increasing the overall dose given to the first object and the second object.

It is further preferred that the imaging system is adapted for performing a pre-acquisition step for acquiring projections sufficient to determine the region within the second object in which the first object is present, and that the polychromatic radiation source is adapted for illuminating only the determined region such that truncated projections are acquired, which are sufficient to reconstruct the determined region. This allows to determine the region within the second object in which the first object is present and ensures therefore that only the determined region is illuminated such that truncated projections are acquired, which are sufficient to reconstruct the determined region. Thus, it can be ensured that the dose applied to the object is not larger than necessary for reconstructing the first object.

The adaptations of the imaging system and the polychromatic radiation source can be realized at the imaging system and the polychromatic radiation source itself or at control units controlling the imaging system and/or the polychromatic radiation source.

The kind of projections, i.e. the acquisition geometry, needed for reconstructing an object, i.e. which is sufficient to reconstruct the first object or the determined region, is known, for example, from sufficiency conditions.

A sufficiency condition is, for example, that the first object is located completely within the beam of the polychromatic radiation source during imaging of the first object, i.e. that the first object is always, i.e. for each projection direction, completely illuminated during a measurement. This sufficiency condition is preferentially achieved by using an active or passive collimator. An active collimator adapts the beam of the polychromatic radiation source such that only the first object is always within the beam of the polychromatic radiation source, preferentially including a safety margin in order to ensure that the first object is always within the radiation beam of the polychromatic radiation source. A passive collimator collimates the radiation beam of the polychromatic radiation source such that the dimensions of the radiation beam are fixed during the measurement and that the first object is always within the radiation beam during the measurement.

If the object is a vessel or a casing containing a substance, for example, a vessel of a human heart, the substance is preferentially a contrast agent, for example, iodine or an iodine based contrast agent or an gadolinium based contrast agent.

A corresponding imaging method and a corresponding computer program are defined in claims 8 and 10. A corresponding image generation device, a corresponding image generation method and a corresponding computer program for generating an image of an object are defined in claims 7, 9 and 11. Preferred embodiments of the invention are defined in the dependent claims.

It shall be understood that the imaging system of claim 1, the corresponding image generation device of claim 7, the corresponding imaging method of claim 8, the corresponding image generation method of claim 9 as well as a corresponding computer programs of claims 10 and 11 have corresponding preferred embodiments as defined in the dependent claims.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
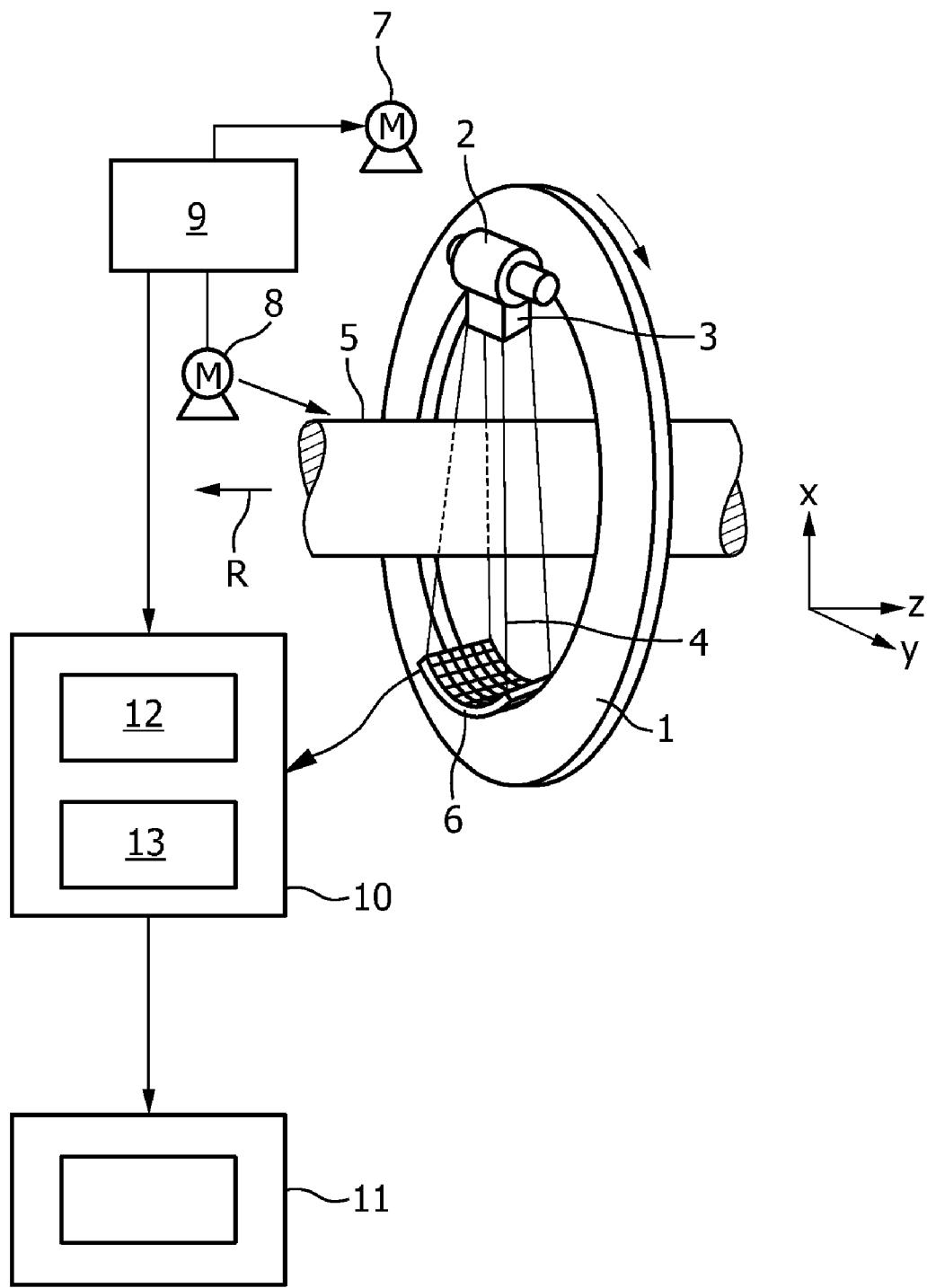
FIG. 1 shows a diagrammatic representation of an imaging system in accordance with the invention.

The imaging system shown in FIG. 1 is a computed tomography system (CT system). The CT system includes a gantry 1 which is capable of rotation about an axis of rotation R which extends parallel to the z direction. The polychromatic radiation source 2, which is in this embodiment an X-ray tube emitting polychromatic X-ray radiation, is mounted on the gantry 1. The X-ray source 2 is provided with a collimator device 3 which forms in this embodiment a conical radiation beam 4 from the radiation produced by the X-ray tube 2. The radiation traverses an object (not shown), such as a patient or vessels of the human heart, in a region of interest in an examination zone 5, which is in this embodiment cylindrical. After having traversed the examination zone 5, the X-ray beam 4 is incident on an energy-resolving radiation detector, which is in this embodiment an energy-resolving X-ray detector unit 6 being a two-dimensional detector mounted an the gantry 1. The imaging system comprises a driving device having two motors 7, 8. The gantry 1 is driven at a preferably constant but adjustable angular speed by the motor 7. The further motor 8 is provided for displacing the object, for example a patient, who is arranged on a patient table in the examination zone 5, parallel to the direction of the axis of rotation R or the z axis. These motors 7, 8 are controlled by a control unit 9, for instance, such that the radiation source 2 and the examination zone move relative to each other along a helical trajectory. However, it is also possible that the object or the examination zone 5 is not moved, but that only the X-ray source 2 is rotated, i.e., that the radiation source moves along a circular trajectory relative to the object. Furthermore, in another embodiment the collimator device 3 can be adapted for forming a fan beam, and the energy-resolving X-ray detector unit can also be a one-dimensional detector.

Energy-resolving X-ray detectors work, for example, on the principle of counting the incident photons and output a signal that shows the number of photons per energy in a certain energy area. Such an energy-resolving detector is, for instance, described in Llopart, X., et al. "First test measurements of a 64 k pixel readout chip working in a single photon counting mode", Nucl. Inst. and Meth. A, 509 (1-3): 157-163, 2003 and in Llopart, X., et al., "Medipix2: A 64-k pixel readout chip with 55 mum square elements working in a single photon counting mode", IEEE Trans. Nucl. Sci. 49(5): 2279-2283, 2002. Preferably, the energy-resolving detector is adapted such that it provides at least three energy resolved detection signals for at least three different energy bins. However, it is advantageous to have an even higher energy resolution in order to enhance the sensitivity and noise robustness of the CT imaging system.

The data acquired by the detector unit 6 are provided to an image generation device 10 for generating an image at least of one of the object and a substance, which might be present within the object, for example, of a contrast agent within the vessels of a human heart.

The reconstructed image can finally be provided to a display 11 for displaying the image. Also the image generation device is preferably controlled by the control unit 9.

A substance within the object is preferentially a contrast agent, for example, based on gadolinium or iodine.

In the following, an embodiment of an imaging method for imaging an object in accordance with the invention will be described in more detail.

At first, the X-ray source 2 rotates around the axis of rotation R or the z direction, and the object is not moved, i.e. the X-ray source 2 travels along a circular trajectory around the object. In another embodiment, the X-ray source can move along another trajectory, for example, a helical trajectory, relative to the object. The X-ray source 2 emits X-ray radiation traversing the object, in which in this embodiment a substance is present. The substance is, for example, a contrast agent, like an iodine or gadolinium based contrast agent, which has been injected in advance. The object is, for example, a vessel of a human heart, wherein the contrast agent is present within this vessel, after the contrast agent has been injected. The X-ray radiation, which has passed the object and the substance within the object, is detected by the detector 6, which generates detection signals. Detection signals, which correspond to the same position of the X-ray source 2 and the detector 6 relative to the object and which have been acquired at the same time, form a projection. The acquisition geometry is adapted such that truncated projections are acquired.

Truncated projections and non-truncated projections will now be described exemplarily in more detail with respect to FIGS. 2a, 2b, 3a, 3b.

Figure 2A:
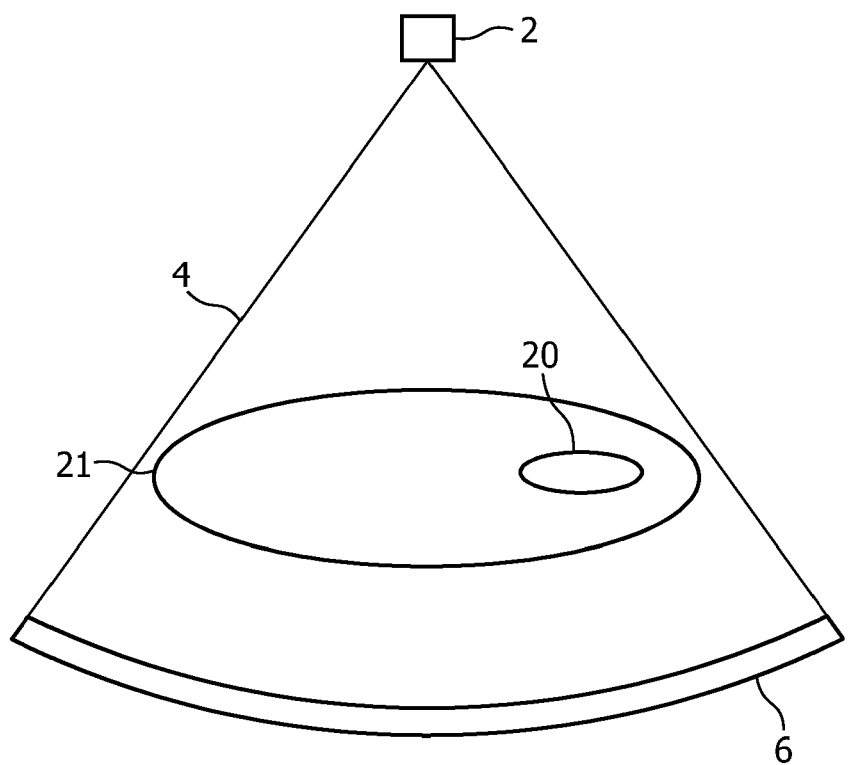
FIG. 2a shows schematically an acquisition geometry for acquiring non-truncated projections.
Figure 2B:
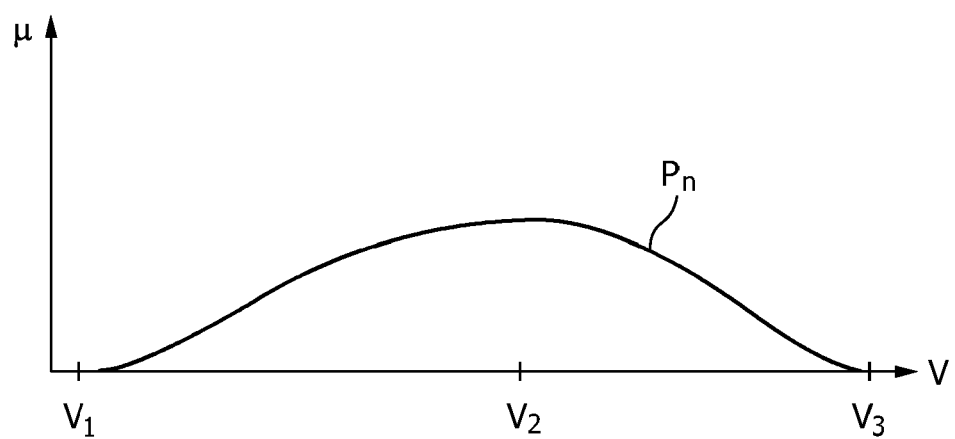
FIG. 2b shows schematically a non-truncated projection.

FIG. 2a shows schematically an acquisition geometry for acquiring non-truncated projections. The beam 4, which is emitted from the radiation source 2, is detected by the detector 6 after having traversed a first object 20 and a second object 21. The detector 6 and the beam 4 are dimensioned such that the second object 21, in which the first object 20 is present, is located completely within the beam 4. A corresponding non-truncated projection $P_n$ is schematically shown in FIG. 2b, in which the absorption µ is shown depending on a position v on the detector 6. At position $v_1$ and at position $v_3$ the beam 4 has not traversed the object 21 so that the absorption µ is zero. At the position $v_2$ the corresponding X-ray of the beam 4 has traversed the first object 21 along a pass being the longest possible pass through the first object 21 so that the absorption µ comprises a maximum at this position $v_2$.

Figure 3A:
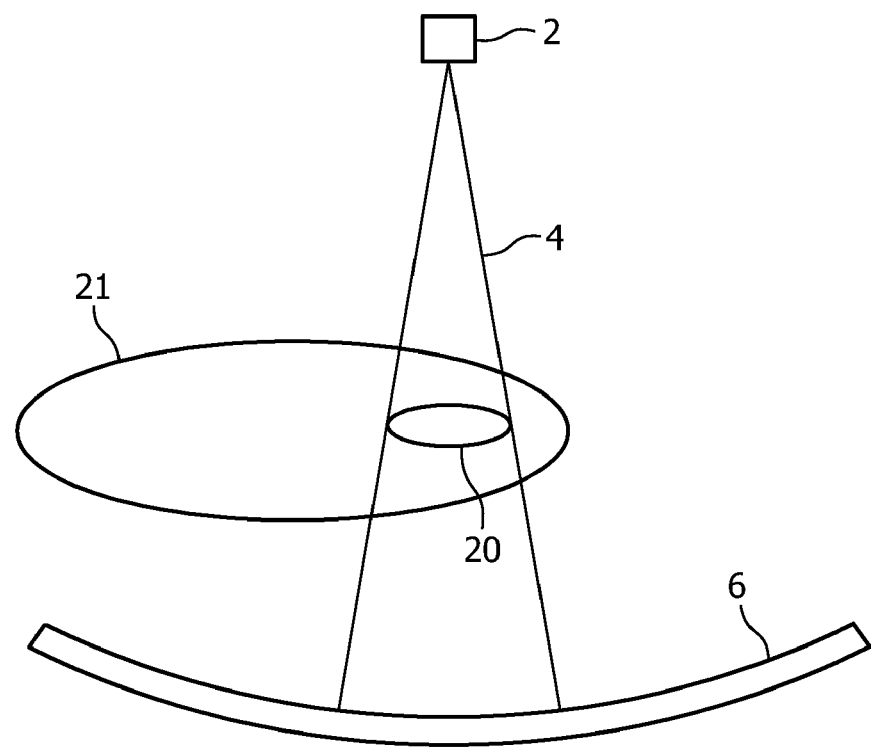
FIG. 3a shows schematically an acquisition geometry for acquiring truncated projections.
Figure 3B:
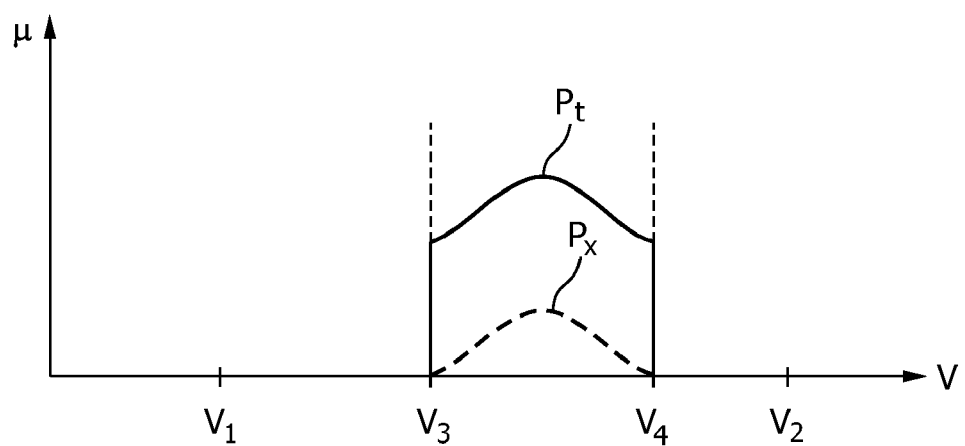
FIG. 3b shows schematically a truncated projection and a non-truncated projection in accordance with the invention.

FIG. 3a shows schematically an acquisition geometry for acquiring truncated projections. The radiation source 2 generates a radiation beam 4 traversing the first object 20 and the second object 21, wherein the radiation beam 4 is detected by the detector 6 after traversing the first object 20 and the second object 21. The radiation beam 4 is dimensioned such that the first object 20 is completely located within the radiation beam 4. The radiation beam 4 is further dimensioned such that projections are acquired which are sufficient to reconstruct the first object 20. Furthermore, the radiation beam 4 is dimensioned such that the second object 21 is not completely located within the radiation beam 4. It is preferred, that the radiation beam 4 is dimensioned such that the dose applied to the second object 21 is as small as possible, while still acquiring projections sufficient to reconstruct the first object 20. FIG. 3b shows schematically a truncated projection $P_t$, which can be acquired by using the acquisition geometry shown in FIG. 3a. FIG. 3b shows the absorption µ depending on a position v on the detector 6. At the detector positions $v_1$ and $v_2$ no radiation has been detected and the detected absorption µ is therefore zero. Since, in comparison to the projection $P_n$ shown in FIG. 2b, in the projection $P_t$ projection data are missing and since the projection $P_t$ comprises steps at the positions $v_3$ and $v_4$, a reconstruction of the first object 20 using truncated projections, like the projection $P_t$, as performed by known imaging systems yields artifacts in the corresponding reconstructed image.

In FIGS. 2a, 2b, 3a, 3b and in the corresponding description truncated and non-truncated projections have been described exemplarily within one plane perpendicular to the z axis or the axis of rotation R. In this embodiment, the detector 6 is a two-dimensional detector and the beam 4 is a cone beam. Therefore, two-dimensional projections are acquired. In this embodiment, a non-truncated projection is therefore a projection, which is, for example, also along the z direction not truncated.

In accordance with the invention, non-truncated projections are determined from the acquired truncated projections by the calculation unit 12. In order to determine such non-truncated projections, a k-edge component of the substance within the first object 20 is determined from the truncated projections, i.e. from the detection signals. This will now be explained in more detail.

Figure 4:
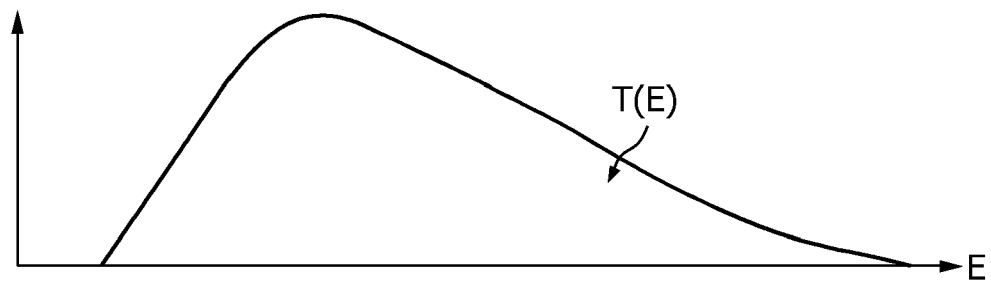
FIG. 4 shows exemplarily a spectrum of a polychromatic X-ray source.

The input to the calculation unit 12 are energy-resolved detection signals $d_i$ for a plurality, at minimum 3, energy bins $b_i$. Each energy bin $b_i$ has a known spectral sensitivity $D_i(E)$. Furthermore, the emission spectrum $T(E)$ of the polychromatic X-ray tube 2 is generally known or can be measured in advance. An example of such an emission spectrum $T(E)$ of a polychromatic X-ray tube is schematically shown in FIG. 4. In the image generation device 10, in particular, in the calculation unit 12, the generation of the detection signals $d_i$ is modeled as a linear combination of the photo-electric effect with spectrum $P(E)$, the Compton effect with spectrum $C(E)$, and k-edge effect of the substance with a k-edge in the interesting energy range and spectrum $K(E)$. In other embodiment, if a substance, like a contrast agent, is not present within the object, the generation of the detection signals $d_i$ is modeled as a linear combination of the photo-electric effect, the Compton effect and the k-edge effect of the object.

Figure 5:
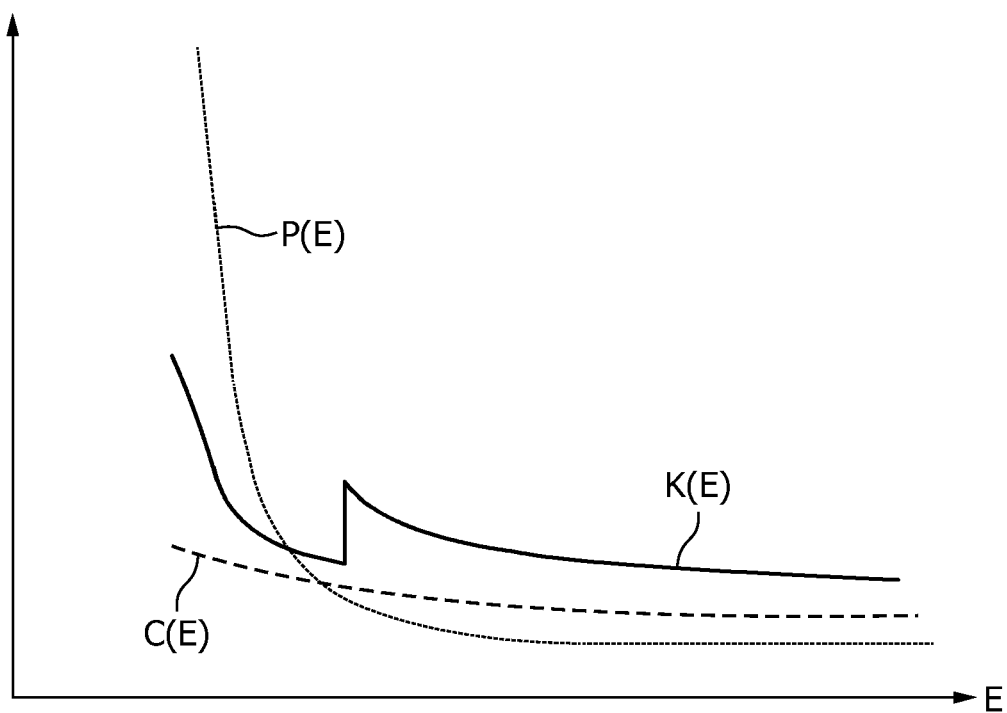
FIG. 5 shows exemplarily spectra of a photo-electric effect, a Compton effect and of a substance within an object.

Spectra P(E), C(E) and K(E) are exemplarily shown in FIG. 5.

The generation of the detection signals, and therefore of the truncated projections, can be modelled by following linear system:

$$d_i = \int dE\, T(E) D_i(E) \exp(-(\rho_{photo} P(E) + \rho_{Compton} C(E) + \rho_{k\text{-}edge} K(E))), \quad (1)$$

wherein $\rho_{photo}$, $\rho_{compton}$ and $\rho_{k\text{-}edge}$ are the density length products of the photo-electric component, the Compton component and the k-edge component, respectively.

Since at least three detection signals $d_1$, $d_2$, $d_3$ are available for the at least three energy bins $b_1$, $b_2$, $b_3$ of the detector 6, a system of at least three equations is formed having three unknowns, which are the three density length products, which can thus be solved with known numerical methods in the calculation unit 12. If more than three energy bins are available, it is preferred to use a maximum likelihood approach that takes the noise statistics of the measurements into account. Generally, three energy bins are sufficient. In order to increase the sensitivity and noise robustness, however, it is preferred to have more detection signals for more energy bins. Each energy bin comprises another spectral sensitivity $D_i(E)$.

Since, for example, by using equation (1), for each detection signal, which detects an X-ray, which has traversed the substance within the first object 20, a k-edge density length product $\rho_{k\text{-}edge}$ is determined, since the density length product $\rho_{k\text{-}edge}$ of the k-edge component comprises only values at detector positions, at which an X-ray has been detected, which has traversed the substance, and since the radiation beam 4 is shaped such that the first object 20 containing the substance is completely located within this radiation beam 4, the determined density length products $\rho_{k\text{-}edge}$ of the k-edge component form a non-truncated projection $P_x$, which is schematically shown in FIG. 3b.

The determined non-truncated projections are transmitted to the reconstruction unit 13. Since the X-ray source 2 moves relative to the object, the detection signals, and therefore the determined non-truncated projections, correspond to X-rays having traversed the object and the substance in different angular directions. Thus, a k-edge image can be reconstructed by using conventional CT reconstruction methods, like a filtered backprojection of the density length products $\rho_{k\text{-}edge}$ forming the non-truncated projections. Since the reconstruction unit 13 only uses non-truncated projections, an reconstructed image of the first object, i.e. of the substance within the first object, comprises less artefacts than images, which have been reconstructed by known imaging system using truncated projections.

If the object 20 is, for example, a vessel structure of a human heart and if, for example, the substance within the vessel structure is a contrast agent, like a iodine based or a gadolinium based contrast agent, the contrast agent within the vessel structure of the human heart can be reconstructed, i.e. the vessel structure within the human heart, being in this example the first object 20 (coronary angiography).

Since only the first object 20 has to be illuminated such that projections are acquired sufficient to reconstruct the first object, an acquisition geometry can be used, like the one schematically shown in FIG. 3a, which allows to reduce the overall dose applied to the second object 21, being, for example, a patient, without decreasing the quality of the reconstructed images. Alternatively, the quality of the reconstructed images can be further improved, by increasing the intensity of the radiation beam 4, without increasing the overall dose applied to the second object 21, because, in comparison to the acquisition geometry shown in FIG. 2a, only a smaller part of the second object 21 is illuminated.

While the invention has been illustrated and described in detail in the drawings and foregoing description, such illustration and description are to be considered illustrative or exemplary and not restrictive. The invention is not limited to the disclosed embodiments.

The object, in particular, the first object, can be a whole object or only a part of an object. This part of an object can be a field of interest, which is predetermined, for example, by user. Instead of determining the k-edge component of a substance within an object, the k-edge component of the object itself can be determined and used to determine non-truncated projections.

The object can be any object, in particular, the object can also be a technical object. Furthermore, the substance can be any substance, whose k-edge component can be determined by the imaging system, in particular, whose k-edge component is located within an energy range detectable by the imaging system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An imaging system for imaging an object, comprising:
   a polychromatic radiation source for emitting polychromatic radiation,
   an energy-resolving radiation detector for obtaining energy-resolved detection signals in at least three energy bins depending on the radiation after passing through the object,
   a driving device for moving the object and the radiation source relatively to each other, in order to acquire truncated projections from different directions, wherein the truncated projections comprise the detection signals,
   a calculation unit for determining a k-edge component of at least of one of the object and a substance within the object from the truncated projections and for determining non-truncated projections from the determined k-edge component,
   a reconstruction unit for reconstructing the object using the non-truncated projections.

2. The imaging system as claimed in claim 1,
   wherein the calculation unit is adapted for determining the k-edge component by solving a system of equations describing detection signals of the truncated projections as a combination of the k-edge effect at least of one of the object or of a substance within the object, the photo-electric effect and the Compton effect, each contributing with a corresponding component to the detection signals.

3. The imaging system as claimed in claim 2,
wherein the calculation unit is adapted for using a model which takes account of an emission spectrum of the radiation source and the spectral sensitivity of the detector.

4. The imaging system as claimed in claim 1,
wherein the polychromatic radiation source is a polychromatic X-ray source, and wherein the energy-resolving radiation detector is an energy-resolving X-ray detector.

5. The imaging system as claimed in claim 1,
wherein the imaging system is adapted for imaging the object being a first object present within a second object,
wherein the polychromatic radiation source is adapted for illuminating only the first object such that truncated projections are acquired, which are sufficient to reconstruct the first object.

6. The imaging system as claimed in claim 5,
wherein the imaging system is adapted for performing a pre-acquisition step for acquiring projections sufficient to determine the region within the second object in which the first object is present, and
wherein the polychromatic radiation source is adapted for illuminating only the determined region such that truncated projections are acquired, which are sufficient to reconstruct the determined region.

7. An image generation device for generating an image of an object, the image generation device being provided with truncated projections comprising detection signals in at least three energy bins, the truncated projections being acquired from different directions by moving the object and a polychromatic radiation source for emitting polychromatic radiation relatively to each other, the detection signals being obtained depending on the radiation after passing through the object by an energy resolving radiation detector, wherein the image generation device comprises:
  a calculation unit for determining a k-edge component of at least of one of the object and a substance within the object from the truncated projections and for determining non-truncated projections from the determined k-edge component,
  a reconstruction unit for reconstructing the object using the non-truncated projections.

8. An imaging method for imaging an object, comprising the steps of:
  emitting polychromatic radiation by a polychromatic radiation source,
  obtaining energy-resolved detection signals in at least three energy bins depending on the radiation after passing through the object by an energy-resolving radiation detector,
  moving the object and the radiation source relatively to each other by a driving device, in order to acquire truncated projections from different directions, wherein the truncated projections comprise the detection signals,
  determining a k-edge component of at least of one of the object and a substance within the object from the truncated projections and for determining non-truncated projections from the determined k-edge component by a calculation unit,
  reconstructing the object using the non-truncated projections by a reconstruction unit.

9. A computer program for imaging an object, comprising program code means for causing a computer to carry out the steps of an imaging method as claimed in claim 8.

10. An image generation method for generating an image of an object, the image generating method being provided with truncated projections comprising energy-resolved detection signals in at least three energy bins, the truncated projections being acquired from different directions by moving the object and a polychromatic radiation source for emitting polychromatic radiation relatively to each other, the detection signals being obtained depending on the radiation after passing through the object by an energy resolving radiation detector, wherein the image generation method comprises the steps of:
  determining a k-edge component of at least of one of the object and a substance within the object from the truncated projections,
  determining non-truncated projections from the determined k-edge component by a calculation unit,
  reconstructing the object using the non-truncated projections by a reconstruction unit.

11. A computer program for generating an image of an object, comprising program code means for causing a computer to carry out the steps of an image generation method as claimed in claim 10.

* * * * *